United States Patent [19]
Chang et al.

[11] Patent Number: 5,453,556
[45] Date of Patent: Sep. 26, 1995

[54] OLIGOMERIZATION PROCESS FOR PRODUCING SYNTHETIC LUBRICANTS

[75] Inventors: Clarence D. Chang, Princeton; Scott Han, Lawrenceville, both of N.J.; Jose G. Santiesteban, Yardley, Pa.; Margaret M. Wu, Skillman, N.J.; Yusheng Xiong, Newtown, Pa.

[73] Assignee: Mobil Oil Corporation, Fairfax, Va.

[21] Appl. No.: 264,089

[22] Filed: Jun. 22, 1994

[51] Int. Cl.$^6$ .................................................. C07C 2/02
[52] U.S. Cl. ...................... 585/524; 585/502; 585/520; 585/523; 585/530; 585/531
[58] Field of Search .................................. 585/502, 520, 585/523, 524, 530, 531

[56] References Cited

U.S. PATENT DOCUMENTS 3,691,144 9/1972 Zuech .................................... 585/520
5,113,034 5/1992 Soled et al. ............................ 585/520
5,264,642 11/1993 Wu ........................................ 585/530

Primary Examiner—Sharon A. Gibson
Assistant Examiner—E. D. Irzinski
Attorney, Agent, or Firm—Alexander J. McKillop; Dennis P. Santini; Lori F. Cuomo

[57] ABSTRACT

There is provided an oligomerization process. The process involves the use of a catalyst comprising an acidic solid. The acidic solid may comprise a Group IVB metal oxide, such as zirconia, modified with an oxyanion of a Group VIB metal, such as tungsten. The oligomers produced by this process may be hydrogenated to produce thermally stable lubricants and lubricant additives.

20 Claims, No Drawings

OLIGOMERIZATION PROCESS FOR PRODUCING SYNTHETIC LUBRICANTS

BACKGROUND

There is provided an oligomerization process. The process involves the use of a catalyst comprising an acidic solid. The acidic solid may comprise a Group IVB metal oxide, such as zirconia, modified with an oxyanion of a Group VIB metal, such as tungsten. The oligomers produced by this process may be hydrogenated to produce thermally stable lubricants and lubricant additives.

Efforts to improve upon the performance of natural mineral oil based lubricants by the synthesis of oligomeric hydrocarbon fluids have been the subject of important research and development in the petroleum industry for a large number of years and have led to the introduction of a number of superior polyalpha-olefin (PAO) synthetic lubricants produced by the oligomerization of alpha-olefins or 1-alkenes. In terms of lubricant property improvement, the thrust of the industrial research effort on synthetic lubricants has been toward fluids exhibiting useful viscosities over a wider range of temperature, i.e., improved viscosity index (VI), while also showing lubricity, thermal and oxidative stability and pour point equal to or better than mineral oil. These new synthetic lubricants exhibit lower friction characteristics and are therefore capable of increasing mechanical efficiency of various types of equipment including engines, transmissions, worm gears and traction drives, doing so over a wider range of operating conditions than mineral oil lubricants.

PAO lubricants are often formulated with additives to enhance those properties for specific applications. Among the more commonly used additives are oxidation inhibitors, rust inhibitors, metal passivators, antiwear agents, extreme pressure additives, pour point depressants, detergent-dispersants, viscosity index (VI) improvers, foam inhibitors and the like. This aspect of lubricant technology is described in *Kirk-Othmer Encyclopedia of Chemical Technology*, 3rd ed., 14, 477–526, to which reference is made for a description of the use of such additives.

PAOs useful as synthetic base stocks or functional fluids may be synthesized by homogeneous catalysts, such as promoted $BF_3$ or $AlCl_3$ catalysts. The synthesis of PAOs with a promoted $BF_3$ catalyst is discussed in the Theriot et al. U.S. Pat. No. 5,171,905. The PAO processes using homogeneous catalysts always include a complicated and tedious catalyst separation step. For example, the promoted $BF_3$ or $AlCl_3$ catalyst is usually deactivated and destroyed by washing with sodium hydroxide, dilute acid and water consecutively. This separation step generates waste and is tedious. Therefore, it would be advantageous to use a solid and regenerable catalyst which can be separated easily from product and regenerated for reuse.

SUMMARY

There is provided a process for oligomerizing olefins, said process comprising contacting at least one olefin having at least 6 carbon atoms under sufficient oligomerization reaction conditions with a catalyst comprising an acidic solid comprising a Group IVB metal oxide modified with an oxyanion of a Group VIB metal.

There is also provided a process for producing a synthetic lubricant composition, said process comprising the steps of:

(a) contacting at least one olefin under sufficient oligomerization reaction conditions with a catalyst comprising an acidic solid comprising a Group IVB metal oxide modified with an oxyanion of a Group VIB metal;

(b) distilling the product of step (a) under conditions sufficient to remove unreacted olefin monomer therefrom; and (c) hydrogenating the oligomers from step (b) under conditions sufficient to remove olefinic unsaturation therefrom.

EMBODIMENTS

Olefins suitable for use as starting material in the present process include those olefins containing from 6 to about 20 carbon atoms. These olefins may be straight chain olefins, such as hexene, octene, decene, dodecene and tetradecene or branched chain olefins such as 4-methyl-1-pentene. The olefins may come from a variety of sources, such as olefin-containing refinery feedstocks or effluents. The olefins may be alpha olefins or internal olefins. However, the olefins used in this process are preferably alpha olefinic as, for example, 1-hexene to 1-hexadecene and more preferably 1-octene to 1-tetradecene, or mixtures of such olefins.

Olefinic feedstocks suitable for use in the present invention include numerous olefinic streams produced by petroleum refining operations, for example, a cracking operation. In a particular cracking operation, a cracked olefinic stream such as an olefinic gasoline boiling range fraction is produced from a delayed coker process unit. Delayed coking processes are taught in U.S. Pat. No. 3,917,564 to Meyers and U.S. Pat. No. 4,874,505 to Bartilucci et al., both of which patents are incorporated herein by reference.

Suitable olefinic feedstocks are also produced as byproducts in catalytic dewaxing processes. An example of such a process is described in U.S. Pat. No. 4,922,048, which patent is incorporated herein by reference.

Suitable olefinic feedstocks may also be produced during oligomerization processes, such as MOGD and MOGDL, which are described more fully hereinafter.

Recent developments in zeolite catalysts and hydrocarbon conversion methods and apparatuses have created interest in utilizing olefinic feedstocks for producing heavier hydrocarbons, such as $C_5+$ gasoline, distillate or lubes. These developments form the basis of the Mobil olefins to gasoline/distillate (MOGD) method and apparatus, and the Mobil olefins to gasoline/distillate/lubes (MOGDL) method and apparatus.

In MOGD and MOGDL, olefins are catalytically converted to heavier hydrocarbons by catalytic oligomerization using an acid crystalline zeolite, such as a zeolite catalyst having the structure of ZSM-5. Process conditions can be varied to favor the formation of either gasoline, distillate or lube range products. U.S. Pat. Nos. 3,960,978 and 4,021,502 to Plank et al. disclose the conversion of $C_2$–$C_5$ olefins alone or in combination with paraffinic components, into higher hydrocarbons over a crystalline zeolite catalyst. U.S. Pat. Nos. 4,150,062; 4,211,640 and 4,227,992 to Garwood et al. have contributed improved processing techniques to the MOGD system. U.S. Pat. No. 4,456,781 to Marsh et al. has also disclosed improved processing techniques for the MOGD system.

Olefinic feedstocks may be obtained from various sources, including from fossil fuel processing streams such as gas separation units, from the cracking of $C_2$-hydrocarbons, such as LPG (liquified petroleum gas) from coal by-products, from various synthetic fuel processing streams, and as by-products from fluid catalytic cracking (FCC) and thermal catalytic cracking (TCC) process units. U.S. Pat. No. 4,100,218 to Chen et al. teaches thermal cracking of ethane to ethylene, with subsequent conversion of ethylene to LPG and gasoline over a zeolite catalyst having the structure of ZSM-5.

The source of the alpha olefins may be from ethylene oligomerization processes. Other sources of alpha olefins include olefins generated in wax-cracking, in a Fischer-Tropsch process, or from coker over-head. Internal olefins may be available from paraffin dehydrogenation, from the conversion of propylene via MOGD or MOGDL, or from isomerized alpha olefins. Especially when the olefin feed comprises internal olefins, optionally in admixture with alpha olefins, the olefins may comprise tetradecene, pentadecene, and/or hexadecene.

In the present oligomerization process, the olefin feed is contacted with the oligomerization catalyst to produce the desired oligomer product. An alpha-olefin feedstock comprising olefins of 6 to 20 carbon atoms, or mixtures of such olefins, is contacted with the oligomerization catalyst under oligomerization conditions, suitably at a reaction temperature between 20° to 250° C., e.g., 50° C. to 250° C. Higher temperatures tend to produce the lower viscosity oligomer products while lower temperatures tend to produce the higher viscosity products. Thus, the viscosity of the oligomer product will depend upon the temperature used in the oligomerization process.

The oligomeric liquid product may comprise $C_{20}$–$C_{100}$ hydrocarbons. The oligomeric product may have a weight average molecular weight between 280 and 15,000, a number average molecular weight between 280 and 5,000, a molecular weight distribution between 1 and 5, and a pour point below −15° C. The viscosity index of the oligomeric product (especially the $C_{26}^+$ oligomers) may be greater than 100.

The catalyst described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, 4, 1727–1735 (1988), the entire disclosures of these publications are expressly incorporated herein by reference.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

An example of this chemical interaction is discussed in the aforementioned article by K. Arata and M. Hino in *Proceedings 9th International Congress on Catalysis*, 4, 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that tungstate-modified zirconia may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., W, in terms of their ability to function as an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic properties of the catalyst.

Suitable sources of the Group IVB metal oxide, used for preparing the present catalyst, include compounds capable of generating such oxides, such as oxychlorides, chlorides, nitrates, oxynitrates, etc., particularly of zirconium or titanium. Alkoxides of such metals may also be used as precursors or sources of the Group IVB metal oxide. Examples of such alkoxides include zirconium n-propoxide and titanium i-propoxide. Sources of a Group IVB metal oxide may be precipitated in the form of zirconium hydroxide, i.e., $Zr(OH)_4$, and hydrated zirconia. This precipitation of zirconium hydroxide or hydrated zirconia may take place separately or concurrently with the precipitation of tungstate. When this precipitation takes place separately, tungstate may be impregnated onto the zirconium hydroxide or hydrated zirconia theoretically by a reaction mechanism discussed hereinafter. The expression, hydrated zirconia, is intended to connote materials comprising zirconium atoms covalently linked to other zirconium atoms via bridging oxygen atoms, i.e., Zr—O—Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis*, 4, 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with an aqueous medium prior to contact with a source of tungstate may be preferable. More particularly, as demonstrated in copending U.S. application Ser. No. 08/095,884, filed Jul. 22, 1993, refluxing hydrated zirconia in an aqueous medium having a pH of greater than or equal to 7 was beneficial. Without wishing to be bound by any theory, it is theorized that the hydrothermally-treated, hydrated zirconia is better because it has higher surface area. It is also theoretically possible that the hydrothermal treatment alters surface hydroxyl groups on the hydrated zirconia, possibly in a manner which promotes a more desirable interaction with the source of tungstate later used.

The hydrothermal conditions may include a temperature of at least 50° C., e.g., at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group IVB metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of 7 or greater, e.g., 9 or greater. Suitable liquid mediums include water, hydroxide solutions (including hydroxides of $NH_4^+$, $Na^+$, $K^+$, $Mg^{2+}$ and $Ca^{2+}$), carbonate and bicarbonate solutions (including carbonates and bicarbonates of $NH_4^+$, $Na^+$, $K^+$, $Mg^{2+}$ and $Ca^{2+}$), pyridine and its derivatives, and alkyl/hydroxyl amines.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate. The oxyanion of the Group VIB metal may optionally be replaced, at least in part, with sulfate.

A co-precipitation technique for preparing the present acidic solid is described in copending U.S. application Ser. No. (Attorney Docket No. 7352).

The present catalyst may be prepared, for example, by a co-precipitation technique or by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.1–24 hours, and more preferably for about 1.0–10 hours. In a most preferred embodiment, calcination is carried out at about 800° C. for about 1 to about 3 hours. An optional hydrogenation component (e.g., Group VIII metal, Group VIIB metal, etc.) may be added after or before the calcination step by techniques known in the art, such as impregnation, coimpregnation, coprecipitation, physical admixture, etc. The hydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperatures may not be needed.

In the present catalyst, of the Group IVB oxides, zirconium oxide is preferred; and of the Group VIB anions, tungstate is preferred.

Qualitatively speaking, elemental analysis of the present catalyst may reveal the presence of Group IVB metal, Group VIB metal and oxygen. The amount of oxygen measured in such an analysis will depend on a number of factors, such as the valence state of the Group IVB and Group VIB metals, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), from 2 to 1000, e.g., from 2 to 300, e.g., from 2 to 100, e.g., from 4 to 30.

The present catalyst is acidic and may be observed as being highly acidic, even to the extent of being a superacid. For example, this catalyst, whether analyzed in the presence or absence of optional components (e.g., hydrogenation/dehydrogenation components) and/or binder materials, may have an acid strength of a superacid as measured by the color change of an appropriate indicator, such as the Hammett indicator. More particularly, the Ho acid strength of the present catalyst may have a value of less than −13, i.e., an "acid strength" of greater than −13. The use of Hammett indicators to measure the acidity of solid superacids is discussed in the Soled et al. U.S. Pat. No. 5,157,199. This Soled et al. patent also describes the Ho acid strength for certain sulfated transition metal superacids. Calcination of the present catalyst at a temperature of greater than 500° C. helps to impart superacidity to the catalyst.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

It is noted that the present catalyst need not contain any sulfate ion (U.S. Pat. No. 4,918,041). It is believed that the present catalyst, especially when free of sulfate ion, is more stable and also is much easier to regenerate than sulfated catalysts, such as the superacid sulfated catalysts referred to in the aforementioned article by K. Arata and M. Hino in *Proceedings 9th International congress on catalysis*, 4, 1727–1735 (1988).

The catalyst may be subjected to a final calcination under conventional conditions in order to dehydrate the catalyst and to confer the required mechanical strength on the catalyst.

It may be desirable to subject the present catalyst to reducing conditions. Benefits of such reducing conditions are demonstrated in copending U.S. application Ser. No. 08/143,716, filed Nov. 1, 1993. For example, the catalytic activity of the catalyst can be improved by contacting the catalyst with hydrogen gas at a temperature ranging from 200° C. to 500° C.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion of pelletizing into the desired finished catalyst particles.

The catalyst may be treated by conventional pre-sulfiding treatments, e.g., by heating in the presence of hydrogen sulfide, to convert oxide forms of the metal components to their corresponding sulfides.

The catalyst, particularly the aged or spent catalyst, can be regenerated by calcination in an oxygen-containing gaseous medium, such as air. Calcination temperature for such regeneration may be as high as 500° C. or even higher. Following such calcination, the catalyst may be treated with hydrogen in the manner described in the aforementioned copending U.S. application Ser. No. 08/143,716. For example, the calcined catalyst may be contacted with $H_2$ at a temperature from about 200° C. to about 300° C.

The present oligomerization reaction may be carried out in a slurry reactor where the catalyst and reactants are mixed and heated to a sufficient reaction temperature, e.g., from 50° C. to 250° C., for a sufficient reaction time, e.g., for a few hours. The catalyst loading in such a slurry reactor may vary from 0.1 wt. % to 10 wt. %. When all starting olefins are converted, the product can be isolated by simple filtration to remove the catalyst. The oligomerization reaction may also be carried out in a fixed-bed reactor. Furthermore, the used catalyst may be reused. If the catalyst is aged, e.g., by poison during the reaction, it may be regenerated by simple calcination in air at 500° C. or higher.

EXAMPLE 1

A tungstate-modified zirconia ($WO_x/ZrO_2$) catalyst was prepared by impregnating ammonium metatungstate (17.5 wt. % W target loading) onto $Zr(OH)_4$. $Zr(OH)_4$ was prepared by dissolving $ZrOCl_2$ in water, precipitating with $NH_4OH$, and subsequently refluxing the precipitate in water. PH was adjusted to ~9. After the impregnation, the catalyst was calcined in flowing dry air at 800° C. for 3 hours. The $WO_x/ZrO_2$ catalyst was pretreated in flowing $H_2$ at 350° C. for 15 hours prior to catalytic testing.

EXAMPLE 2

In a round-bottom flask, 22 grams of 1-decene and 1.06 gram of the catalyst prepared in Example 1 were mixed and heated to 150° C. for 24 hours. The product was isolated by filtering off the solid catalyst at room temperature. The product compositions were analyzed by GC. $C_{30}+$ lube product was isolated by distillation at 110° C./0.05 millitorr to remove unreacted decene and $C_{20}$ light end. The compositions and lube properties were summarized in Table 1.

EXAMPLES 3–5

Examples 3–5 were conducted in a manner similar to Example 2 except for different reaction conditions as summarized in Table 1.

EXAMPLE 6

5.2 cc (24/30 mesh) of the catalyst prepared in Example 1 were tested in a fixed-bed down flow reactor. 1-Decene was fed into the reactor using an Isco pump. Reaction products were collected at reactor exit and analyzed by GC. $C_{30}+$ lube product was isolated by distillation at 110° C./0.05 millitorr to remove unreacted decene and $C_{20}$ light end. The compositions and lube properties were summarized in Table 1.

TABLE 1

| PAO synthesis from 1-decene Reaction over $WO_x/ZrO_2$ Catalyst | | | | | |
|---|---|---|---|---|---|
| Example No. | 2 | 3 | 4 | 5 | 6 |
| Pressure, atm | 1 | 1 | 1 | 1 | 1 |
| Temp., °C. | 150 | 130–150 | 150 | 150 | 150 |
| Time, hrs | 24 | 5 | 6 | 3 | — |
| Feed rate, cc/cc/hr | — | — | — | — | 0.5 |
| Crude product compositions by % | | | | | |
| $C_{10}$ | 12 | 17 | 24 | 31 | 22 |
| $C_{20}$ | 46 | 38 | 45 | 58 | 58 |
| $C_{30}+$ | 42 | 45 | 31 | 11 | 20 |
| $C_{30}+$ fraction lube properties | | | | | |
| V @ 100° C., cS | 5.0 | 5.1 | 4.6 | 9.8 | 7.7 |
| V @ 40° C., cS | 24 | 28 | 30 | 62 | 57 |
| VI | 140 | 110 | 64 | 152 | 110 |

EXAMPLE 7

The procedure of Examples 3–5 was followed except that a different feed was used. The feed for this Example 7 was Neodene, which is an internal and terminal mixture of $C_{14}$ to $C_{19}$ olefins obtained from Shell. Oligomerization at 150°–180° C. produced a pale yellow oil in 65–70% yield. The results are summarized in Table 2.

TABLE 2

| Catalyst, wt. % | 6.8%, 3rd cycle | 6.7%, 7th cycle |
|---|---|---|
| Reaction temp., °C. | 150–200 | 180 |
| Reaction time, hrs. | 5 | 7 |

TABLE 2-continued

| | | |
|---|---|---|
| Product yield | 65% | 70% |
| Viscosity | | |
| @ 100° C., cS | 5.28 | 4.72 |
| @ 40° C., cS | 25.9 | 21.96 |
| VI | 141 | 138 |
| Pour point, °C. | −25 | −28.7 |
| GC analysis | | |
| Dimers, % | 66.8 | 74.0 |
| Trimers, % | 28.0 | 23.1 |
| Tetramers, % | 5.2 | 2.9 |

As indicated by a GC analysis of the product, oligomerization occurred preferentially to the components having double bonds near the chain terminal. The α-olefin component disappeared first, leaving some internal olefin unconverted even after several hours at 180° C. At the higher temperature of 200° C., cracking takes place to a small extent, evidenced by the presence of $C_4$ to $C_{14}$ hydrocarbons in the GC.

What is claimed is:

1. A process for oligomerizing olefins, said process comprising contacting at least one olefin having at least 6 carbon atoms under sufficient oligomerization reaction conditions with a catalyst comprising an acidic solid comprising a Group IVB metal oxide modified with an oxyanion of a Group VIB metal.

2. A process according to claim 1, wherein the olefin is at least one 1-alkene having from 6 to 20 carbon atoms.

3. A process according to claim 1, wherein the olefin is selected from the group consisting essentially of 1-hexene, 1-octene, 1-decene, 1-dodecene, 1-tetradecene or mixtures of these olefins.

4. A process according to claim 1, wherein the olefin comprises 1-decene.

5. A process according to claim 1, wherein said olefin comprises at least one internal olefin.

6. A process according to claim 5, wherein said internal olefin is selected from the group consisting of tetradecene, pentadecene, hexadecene and mixtures thereof.

7. A process according to claim 1, wherein said Group IVB metal is Zr and wherein said Group VIB metal is W.

8. A process according to claim 1, wherein said contacting is at a temperature of from 20° to 250° C. producing an oligomeric liquid lubricant composition comprising $C_{20}$–$C_{100}$ hydrocarbons.

9. A process according to claim 1, wherein said contacting is at a temperature of from 20° to 250° C. producing an olefin oligomer having a weight average molecular weight between 280 and 15,000, number average molecular weight between 280 and 5,000, molecular weight distribution between 1 and 5, and pour point below −15° C.

10. A process according to claim 1, wherein said contacting produces olefin oligomer product having a viscosity index greater than 100.

11. A process for producing a synthetic lubricant composition, said process comprising the steps of:
   (a) contacting at least one olefin under sufficient oligomerization reaction conditions with a catalyst comprising an acidic solid comprising a Group IVB metal oxide modified with an oxyanion of a Group VIB metal;
   (b) distilling the product of step (a) and removing unreacted olefin monomer therefrom; and
   (c) hydrogenating the oligomers from step (b) and removing olefinic unsaturation therefrom.

12. A process according to claim 11, wherein the olefin is at least one 1-alkene having from 6 to 20 carbon atoms.

13. A process according to claim 11, wherein the olefin is selected from the group consisting essentially of 1-hexene, 1-octene, 1-decene, 1-dodecene, 1-tetradecene, 1-hexadecene, or mixtures of these olefins.

14. A process according to claim 11, wherein the olefin comprises 1-decene.

15. A process according to claim 11, wherein said Group IVB metal is Zr and wherein said Group VIB metal is W.

16. A process according to claim 11, wherein said contacting is at a temperature of from 20° to 250° C. producing an oligomeric liquid lubricant composition comprising $C_{20}$–$C_{100}$ hydrocarbons.

17. A process according to claim 11, wherein said contacting is at a temperature of from 50° to 250° C. producing an olefin oligomer having a weight average molecular weight between 280 and 15,000, number average molecular weight between 280 and 5,000, molecular weight distribution between 1 and 5, and pour point below −15° C.

18. A process according to claim 11, wherein said contacting produces olefin oligomer product comprising $C_{26}+$ hydrocarbons having a viscosity index greater than 100.

19. A process according to claim 11, wherein said olefin comprises at least one internal olefin.

20. A process according to claim 19, wherein said olefin comprises at least one olefin selected from the group consisting of tetradecene, pentadecene, and hexadecene.

* * * * *